US00PP26267P2

(12) United States Plant Patent
Kumar

(10) Patent No.: US PP26,267 P2
(45) Date of Patent: Dec. 22, 2015

(54) ***CORDYLINE* PLANT NAMED 'SPRILECFLASH'**

(50) Latin Name: *Cordyline banksii*
Varietal Denomination: Sprilecflash

(71) Applicant: Krishna Bhuvanendra Kumar, Zhejiang (CN)

(72) Inventor: Krishna Bhuvanendra Kumar, Zhejiang (CN)

(73) Assignee: Sprint Horticulture PTY. LTD, Wamberal, New South Wales (AU)

( * ) Notice: Subject to any disclaimer, the term of this patent is extended or adjusted under 35 U.S.C. 154(b) by 157 days.

(21) Appl. No.: 13/999,011

(22) Filed: Dec. 31, 2013

(51) Int. Cl.
*A01H 5/12* (2006.01)

(52) U.S. Cl.
USPC ..... Plt./383

(58) Field of Classification Search
USPC ..... Plt./383
See application file for complete search history.

*Primary Examiner* — Susan McCormick Ewoldt
(74) *Attorney, Agent, or Firm* — C. A. Whealy

(57) ABSTRACT

A new and distinct cultivar of *Cordyline* plant named 'Sprilecflash', characterized by its upright to semi-upright plant habit with leaves initially erect to outwardly arching and slightly recurving; moderately vigorous to vigorous growth habit; long lanceolate variegated leaves with brown and greyed yellow-colored longitudinal stripes; and excellent keeping quality and good garden performance.

2 Drawing Sheets

Botanical designation: *Cordyline banksii.*
Cultivar denomination: 'SPRILECFLASH'.

BACKGROUND OF THE INVENTION

The present invention relates to a new and distinct *Cordyline* plant, botanically known as *Cordyline banksii* and hereinafter referred to by the name 'Sprilecflash'.

The new *Cordyline* plant is a naturally-occurring whole plant mutation of *Cordyline banksii* 'Sprilecpink', disclosed in U.S. Plant Pat. No. 19,213. The new *Cordyline* plant was discovered and selected by the Inventor from within a population of plants of 'Sprilecpink' in a controlled laboratory environment in Zhejiang, China in April, 2008.

Asexual reproduction of the new *Cordyline* plant by micropropagated cuttings in Zhejiang, China since April, 2008 has shown that the unique features of this new *Cordyline* plant are stable and reproduced true to type in successive generations.

SUMMARY OF THE INVENTION

Plants of the new *Cordyline* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sprilecflash'. These characteristics in combination distinguish 'Sprilecflash' as a new and distinct *Cordyline* plant:

1. Upright to semi-upright plant habit with leaves initially erect to outwardly arching and slightly recurving.
2. Moderately vigorous to vigorous growth habit.
3. Long lanceolate variegated leaves with brown and greyed yellow-colored longitudinal stripes.
4. Excellent keeping quality and good garden performance.

Plants of the new *Cordyline* differ primarily from plants of the parent, 'Sprilecpink', in leaf color as plants of 'Sprilecpink' have red purple, greyed purple and brown-colored leaves.

Plants of the new *Cordyline* can be compared to plants of the *Cordyline australis* 'Torbay Dazzler', not patented. In side-by-side comparisons conducted in Mangrove Mountain, New South Wales, Australia, plants of the new *Cordyline* differed primarily from plants of 'Torbay Dazzler' in the following characteristics:

1. Plants of the new *Cordyline* were more freely clumping than plants of 'Torbay Dazzler'.
2. Leaves of plants of the new *Cordyline* and 'Torbay Dazzler' differed in color as plants of 'Torbay Dazzler' had green and yellow variegated leaves with red-colored leaf bases.

Plants of the new *Cordyline* can also be compared to plants of the *Cordyline banksii* 'Sprilecstar', disclosed in U.S. Plant patent application Ser. No. 13/385,875. In side-by-side comparisons conducted in Mangrove Mountain, New South Wales, Australia, plants of the new *Cordyline* differed primarily from plants of the 'Sprilecstar' in leaf color as plants of 'Sprilecstar' had variegated leaves with dark brown, yellow green and greyed orange to greyed yellow-colored longitudinal stripes.

BRIEF DESCRIPTION OF THE PHOTOGRAPHS

The accompanying photographs illustrate the overall appearance of the new *Cordyline* plant showing the colors as true as it is reasonably possible to obtain in colored reproductions of this type. Colors in the photographs may differ slightly from the color values cited in the detailed botanical description which accurately describe the colors of the new *Cordyline* plant.

The photograph on the first sheet comprises side perspective view of typical plants of 'Sprilecflash' grown in containers under full sunlight conditions.

The photograph on the second sheet comprises side perspective view of typical plants of 'Sprilecflash' grown under full sunlight conditions.

DETAILED BOTANICAL DESCRIPTION

The aforementioned photographs and following observations and measurements describe plants grown during the spring, summer and autumn in 17.5-cm containers in an outdoor nursery and in a shadehouse in Mangrove Mountain, New South Wales, Australia and under cultural practices typical of commercial *Cordyline* plant production. During the production of the plants, day temperatures ranged from 20° C. to 30° C. and night temperatures ranged from 15° C. to 22° C. Light levels in the shadehouse ranged from 7,500 to 8,400 foot-candles and light levels under full sunlight conditions ranged from 10,000 to 11,000 foot-candles. Plants were ten months old when the photographs were taken and nine months old when the botanical description was taken. In the following description, color references are made to The Royal Horticultural Society Colour Chart, 2001 Edition, except where general terms of ordinary dictionary significance are used.

Botanical classification: *Cordyline banksii* 'Sprilecflash'.

Parentage: Naturally-occurring whole plant mutation of *Cordyline banksii* 'Sprilecpink', disclosed in U.S. Plant Pat. No. 19,213.

Propagation:

*Type*.—By micropropagated cuttings.

*Time to initiate roots, summer*.—About two weeks at temperatures ranging from 25° C. to 35° C.

*Time to initiate roots, winter*.—About three weeks at temperatures about 18° C.

*Time to produce a rooted young plant, summer*.—About one to two months at temperatures about 25° C.

*Time to produce a rooted young plant, winter*.—About two months at temperatures about 18° C.

*Root description*.—Medium thickness, fleshy; white in color.

*Rooting habit*.—Freely branching; dense.

Plant description:

*Plant and growth habit*.—Upright to semi-upright plant habit with leaves initially erect to outwardly arching and slightly recurving; moderately vigorous to vigorous growth habit; moderate to fast growth rate; plants grown under full sunlight conditions are more upright and produce more leaves per plant than plants grown under shadehouse conditions.

*Plant height, full sunlight-grown plants*.—About 51 cm to 62 cm.

*Plant height, shadehouse-grown plants*.—About 50 cm to 78 cm.

*Plant diameter or spread, full sunlight-grown plants*.—About 53 cm to 74 cm.

*Plant diameter or spread, shadehouse-grown plants*.—About 77 cm to 98 cm.

Leaf description:

*Arrangement*.—Whorled; sessile.

*Length, full sunlight-grown plants*.—About 41 cm to 55 cm.

*Length, shadehouse-grown plants*.—About 53 cm to 71 cm.

*Width, full sunlight-grown plants*.—About 1.3 cm to 1.6 cm.

*Width, shadehouse-grown plants*.—About 1.4 cm to 2.1 cm.

*Shape, full sunlight and shadehouse-grown plants*.—Lanceolate.

*Apex, full sunlight and shadehouse-grown plants*.—Acute.

*Margin, full sunlight and shadehouse-grown plants*.—Entire.

*Cross-sectional profile, full sunlight-grown plants*.—Towards the base, strongly concave, flattening towards the middle of the leaf to the apex.

*Cross-sectional profile, shadehouse-grown plants*.—Towards the base, moderately to strongly concave, flattening towards the middle of the leaf to the apex.

*Texture, upper and lower surfaces, full sunlight and shadehouse-grown plants*.—Leathery; corrugated; glabrous.

*Luster, upper and lower surfaces, full sunlight and shadehouse-grown plants*.—Slightly glossy.

*Venation pattern, full sunlight and shadehouse-grown plants*.—Parallel.

*Color, full sunlight-grown plants*.—Developing leaves, upper surface: Longitudinal stripes, close to 200A and between 154B and 5D; near midrib, occasional streaks, close to 63A. Developing leaves, lower surface: Lighter than 200A and close to 201A. Fully expanded leaves, upper surface: Longitudinal stripes, close to 200A to 200B and 160C. Fully expanded leaves, lower surface: Lighter than 200A and 201A. Venation, upper and lower surfaces: Similar to surface coloration.

*Color, shadehouse-grown plants*.—Developing leaves, upper surface: Longitudinal stripes, close to 200A to 200B and between 154B to 154C and 5B to 5C; near midrib, occasional streaks, close to 63A. Developing leaves, lower surface: Lighter than 200A and close to 201 A. Fully expanded leaves, upper surface: Longitudinal stripes, close to 200B and 160C. Fully expanded leaves, lower surface: Lighter than 200A and 201A. Venation, upper and lower surfaces: Similar to surface coloration.

Flower description: Flower initiation and development has not been observed on plants of the new *Cordyline*.

Disease & pest resistance: Plants of the new *Cordyline* have not been shown to be resistant to pathogens and pests common to *Cordyline* plants.

Keeping quality: Excellent keeping quality; plants of the new *Cordyline* are durable and will maintain good leaf substance indefinitely.

Garden performance: Plants of the new *Cordyline* have been observed to have good garden performance and to tolerate wind, rain, full sunlight and temperatures ranging from about 5° C. to about 45° C.

It is claimed:

1. A new and distinct *Cordyline* plant named 'Sprilecflash' as illustrated and described.

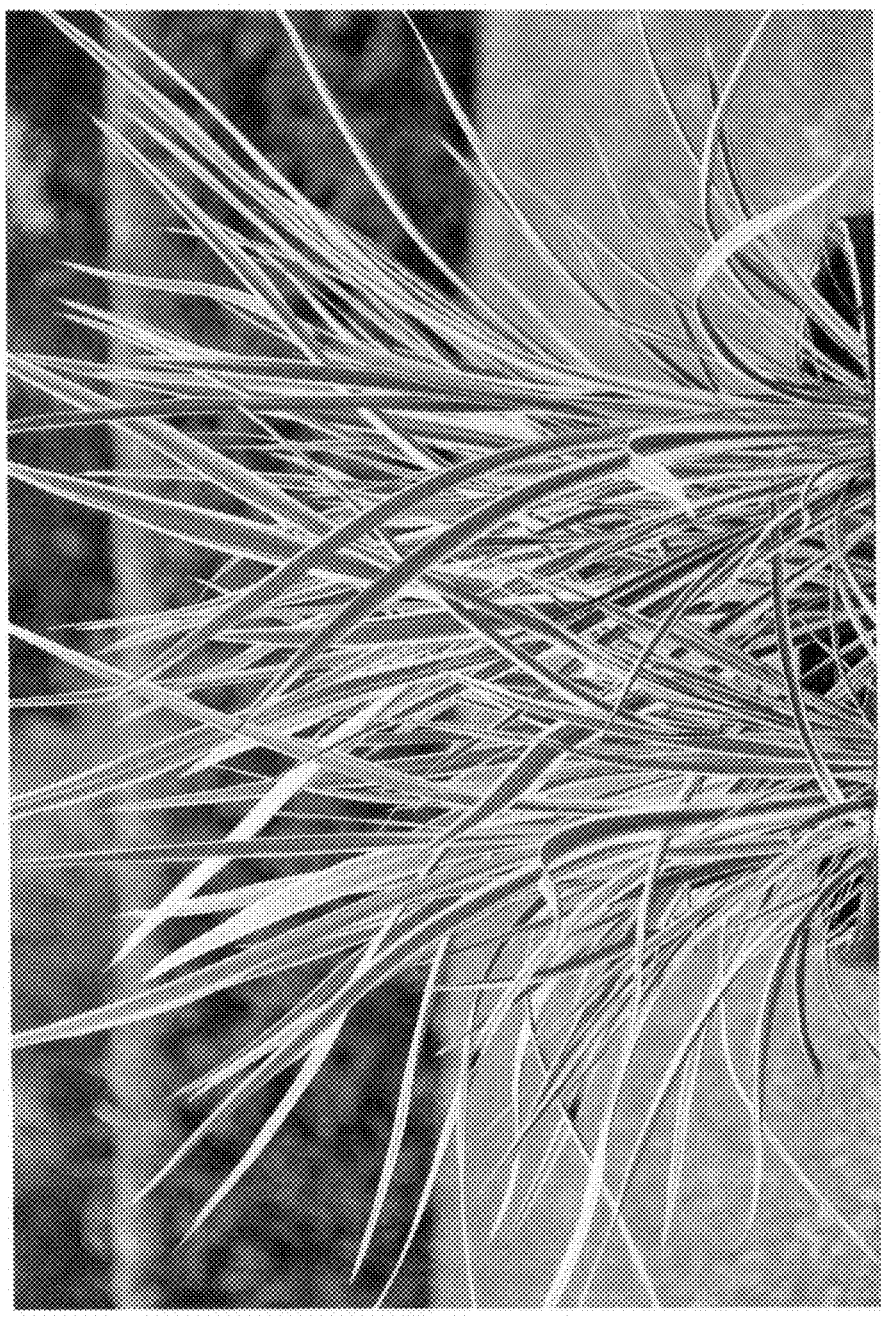

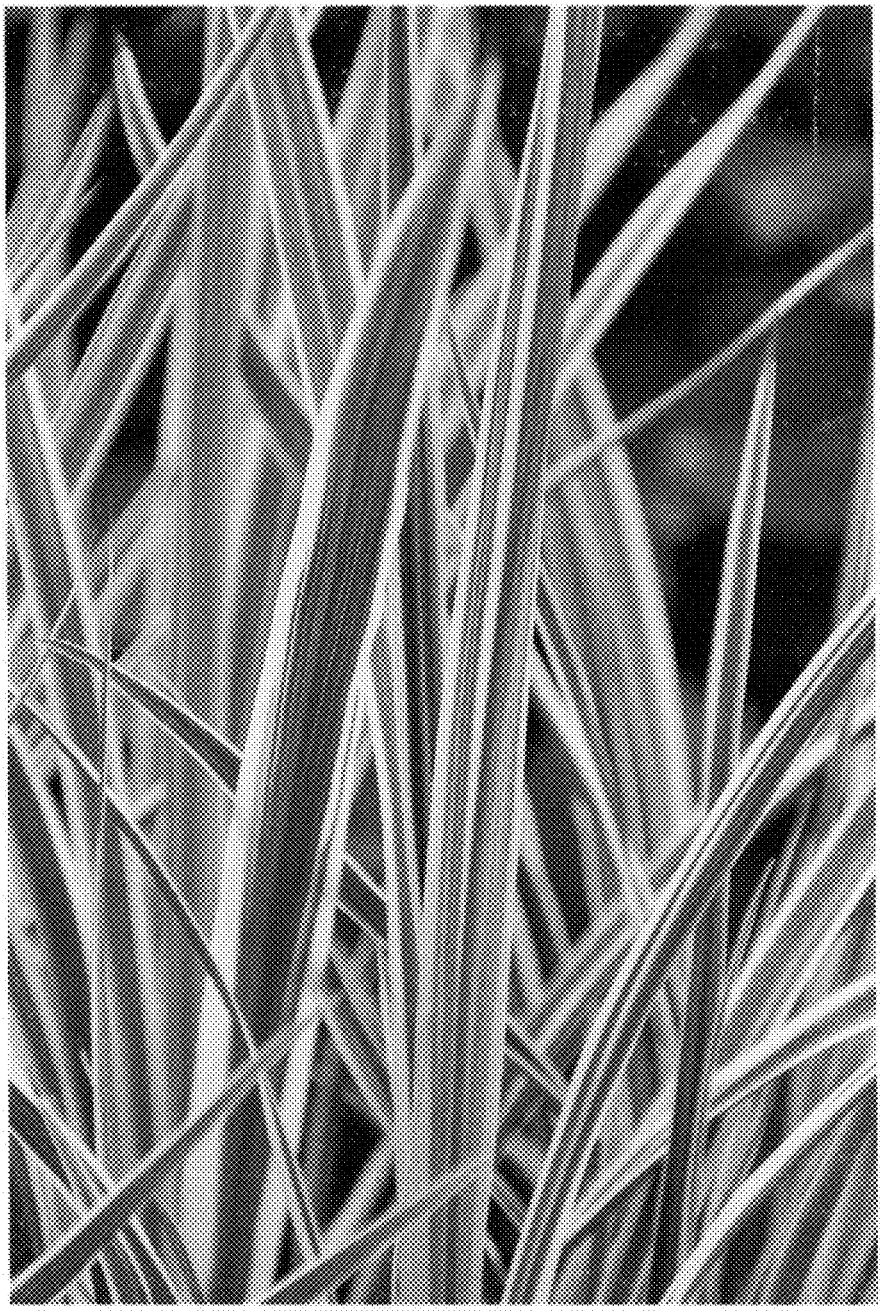

* * * * *